US011124491B2

(12) United States Patent
Petersen

(10) Patent No.: US 11,124,491 B2
(45) Date of Patent: Sep. 21, 2021

(54) PROCESS FOR THE MANUFACTURE OF VORTIOXETINE HBR ALPHA-FORM

(71) Applicant: H. LUNDBECK A/S, Valby (DK)

(72) Inventor: Hans Petersen, Valby (DK)

(73) Assignee: H. Lundbeck A/S, Valby (DK)

(*) Notice: Subject to any disclaimer, the term of this patent is extended or adjusted under 35 U.S.C. 154(b) by 167 days.

(21) Appl. No.: 16/604,313

(22) PCT Filed: Apr. 20, 2018

(86) PCT No.: PCT/EP2018/060192
§ 371 (c)(1),
(2) Date: Oct. 10, 2019

(87) PCT Pub. No.: WO2018/197360
PCT Pub. Date: Nov. 1, 2018

(65) Prior Publication Data
US 2020/0165217 A1 May 28, 2020

(30) Foreign Application Priority Data
Apr. 25, 2017 (DK) .................................. 201700264

(51) Int. Cl.
C07D 295/096 (2006.01)
C07D 295/08 (2006.01)

(52) U.S. Cl.
CPC ....... C07D 295/096 (2013.01); C07D 295/08 (2013.01); C07B 2200/13 (2013.01)

(58) Field of Classification Search
CPC ................................................... C07D 295/06
See application file for complete search history.

(56) References Cited

FOREIGN PATENT DOCUMENTS

| CN | 104 910 099 A | 9/2015 |
| CN | 105 367 515 A | 3/2016 |
| CN | 106 316 986 A | 1/2017 |
| WO | 03/029232 A1 | 4/2003 |
| WO | 2007/144005 A1 | 12/2007 |
| WO | 2008/113359 A2 | 9/2008 |
| WO | WO 2015114395 * | 8/2015 |

OTHER PUBLICATIONS

International Search Report for PCT/EP2018/060192 dated Jun. 14, 2018. 6 pages.
Written Opinion of the International Search Authority for PCT/EP2018/060192. 5 pages.

* cited by examiner

Primary Examiner — Noble E Jarrell
(74) Attorney, Agent, or Firm — Fish & Richardson P.C.

(57) ABSTRACT

A process for the manufacture of vortioxetine HBr α-form is provided.

14 Claims, 17 Drawing Sheets

PROCESS FOR THE MANUFACTURE OF VORTIOXETINE HBR ALPHA-FORM

CROSS REFERENCE TO PRIOR APPLICATIONS

Figure 1:
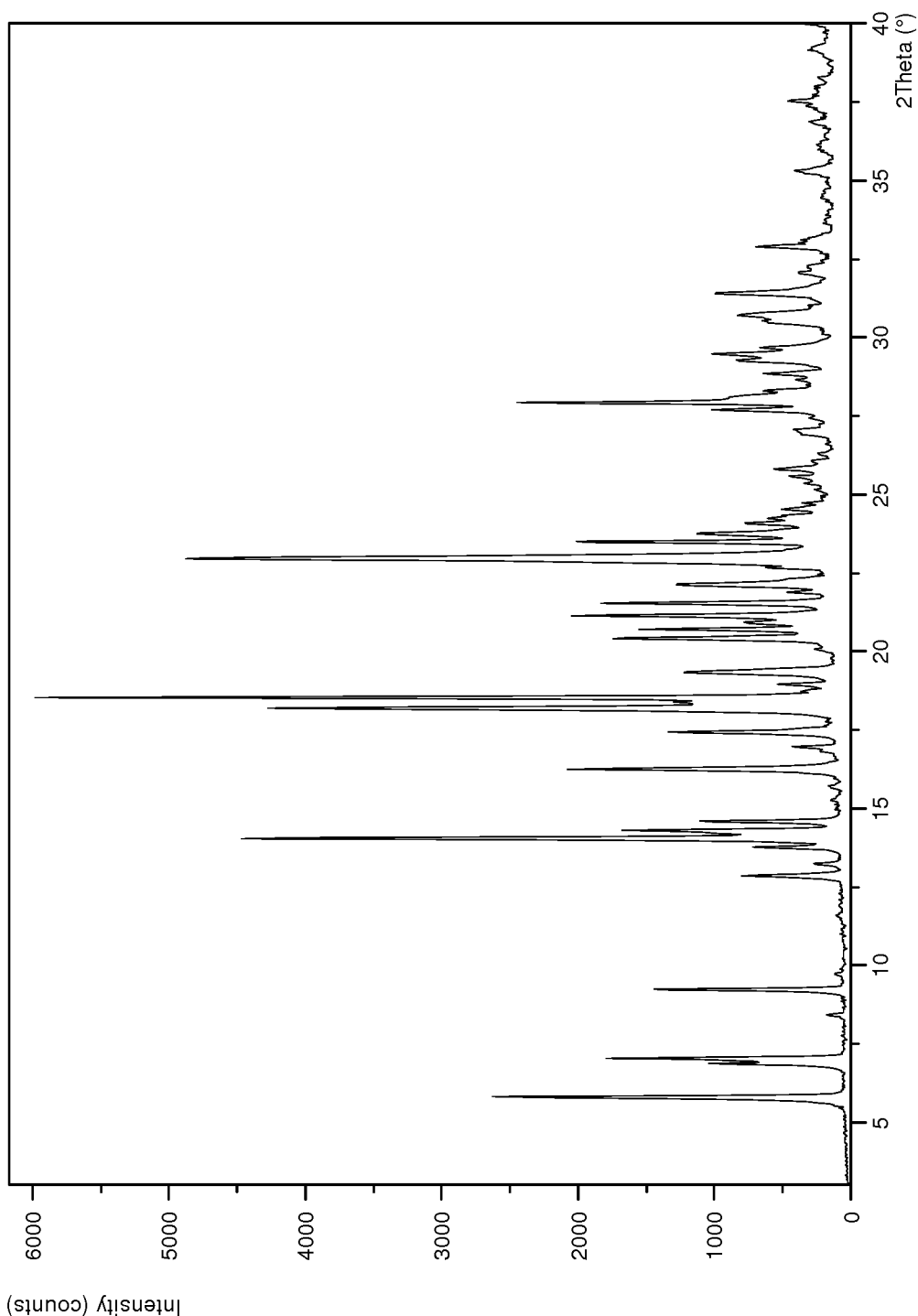

This is a U.S. National Phase application under U.S.C. § 371 of International Patent Application No. PCT/EP2018/060192, filed Apr. 20, 2018, which claims the benefit of DK Application No. PA201700264, filed Apr. 25, 2017. The International Application was published on Nov. 1, 2018 as International Publication No. WO 2018/197360 under PCT Article 21(3). The contents of the above applications are incorporated herein in their entirety.

FIELD OF THE INVENTION

The present invention relates to a manufacturing process for a specific polymorphic form of the vortioxetine HBr salt.

BACKGROUND OF THE INVENTION

International patent applications including WO 03/029232 and WO 2007/144005 disclose the compound 1-[2-(2,4-dimethyl-phenylsulfanyl)-phenyl]-piperazine and pharmaceutically acceptable salts thereof. WHO has since published that vortioxetine is the recommended International Non-proprietary Name (INN) for 1-[2-(2,4-dimethyl-phenylsulfanyl)-phenyl]-piperazine. Vortioxetine was formerly referred to in the literature as Lu AA21004. In September and December 2013 FDA and EMA, respectively, approved vortioxetine for the treatment of major depressive disorder/major depressive episode as the first of a number of regulatory authorities throughout the World under the trade name Brintellix™ or Trintellix™ (United States and Canada).

Vortioxetine is an antagonist on the $5\text{-}HT_3$, $5\text{-}HT_7$ and $5\text{-}HT_{1D}$ receptors, an agonist on the $5\text{-}HT_{1A}$ receptor and a partial agonist on the $5\text{-}HT_{1B}$ receptor and an inhibitor of the serotonin transporter. Additionally, vortioxetine has demonstrated to enhance the levels of the neurotransmitters serotonin, noradrenalin, dopamine, acetylcholine and histamine in specific areas of the brain. These activities are all considered to be of clinical relevance and potentially involved in the mechanism of action of the compound [*J. Med. Chem.*, 54, 3206-3221, 2011; *Eur. Neuropshycopharmacol.*, 18(suppl 4), 5321, 2008; *Eur. Neuropshycopharmacol.*, 21(suppl 4), S407-408, 2011; *Int. J. Psychiatry Clin Pract.* 5, 47, 2012]. The pharmacological profile gives reason to believe that vortioxetine may have a pro-cognitive effect. This notion seems to be supported by clinical evidence where vortioxetine has been shown to have a direct beneficial effect on cognition independent of its antidepressive effects [*Int. Clin. Psychopharm.*, 27, 215-227, 2012; *Int J neurophychopharm* 17, 1557-1567, 2014; *Neuropsychopharm* 40, 2025-2037, 2015].

Vortioxetine is available on the market as film coated tablets containing 5, 10, 15 and 20 mg vortioxetine as the HBr salt and as an oral drop solution comprising 20 mg/ml vortioxetine as the DL lactate salt.

As originally disclosed in WO 2007/144005 and later confirmed in e.g. WO 2014/044721 and EP 2975032 vortioxetine HBr exists in several crystalline forms. As indicated in the FDA label for vortioxetine, the marketed polymorphic form of Trintellix™ is the β-form of the vortioxetine HBr salt. The present application adheres to the polymorph nomenclature as defined in WO 2007/144005.

The Chinese patent applications CN 105367515, CN 106316986 and CN 104910099 disclose processes for the manufacture of vortioxetine HBr α-form. These processes are characterised by a number of features which may limit their industrial applicability. The use of the solvent ethyl acetate in a strongly acidic environment (after addition of aqueous HBr) may result in acid hydrolysis of the solvent. Other processes exploit an alcohol solvate as intermediate from which solvate the alcohol is evaporated to obtain vortioxetine HBr α-form. Such process is time and energy demanding. Still other processes apply several solvents sequentially and long process time which together add to the overall process complexity.

The availability of different polymorphic forms of a pharmaceutical compound may be desirable because the choice of polymorphic form may be used to manipulate factors such as solubility and bioavailability which may again influence the clinical outcome or applicability in various formulation techniques.

The present invention provides a simple manufacturing process for vortioxetine HBr α-form which has high yields and is easy to scale.

SUMMARY OF THE INVENTION

In one embodiment, the present invention provides a process for the manufacture of crystalline vortioxetine HBr α-form (alpha-form), i.e. crystalline vortioxetine HBr characterized by XRPD reflections at 5.85, 9.30, 17.49 and 18.58 (°2θ)(±0.1°), the process comprising the steps of
  a) obtaining a solution of vortioxetine in essentially pure toluene
  b) mixing said solution obtained in step a) with HBr and $C_1$-$C_3$ carboxylic acid at a temperature above 10° C. to obtain mixture b)
  c) collecting the precipitate obtained in step b).

FIGURES

FIG. 1: XRPD diffractogram of the product obtained in Example 1. The x-axis shows the angle °2θ, and the y-axis the intensity in counts.

Figure 2:
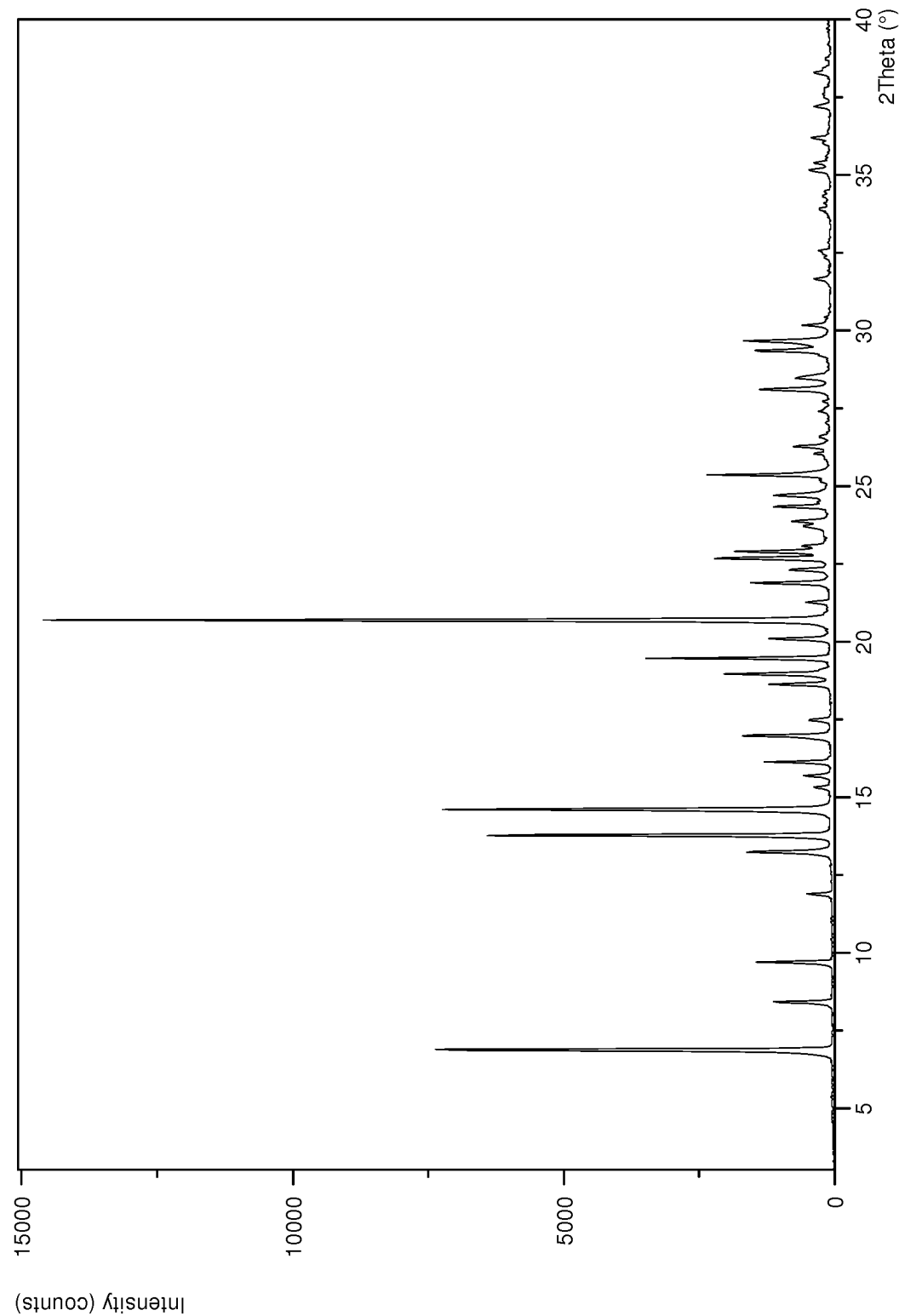

FIG. 2: XRPD diffractogram of the product obtained in Example 2. The x-axis shows the angle °2θ, and the y-axis the intensity in counts.

Figure 3:
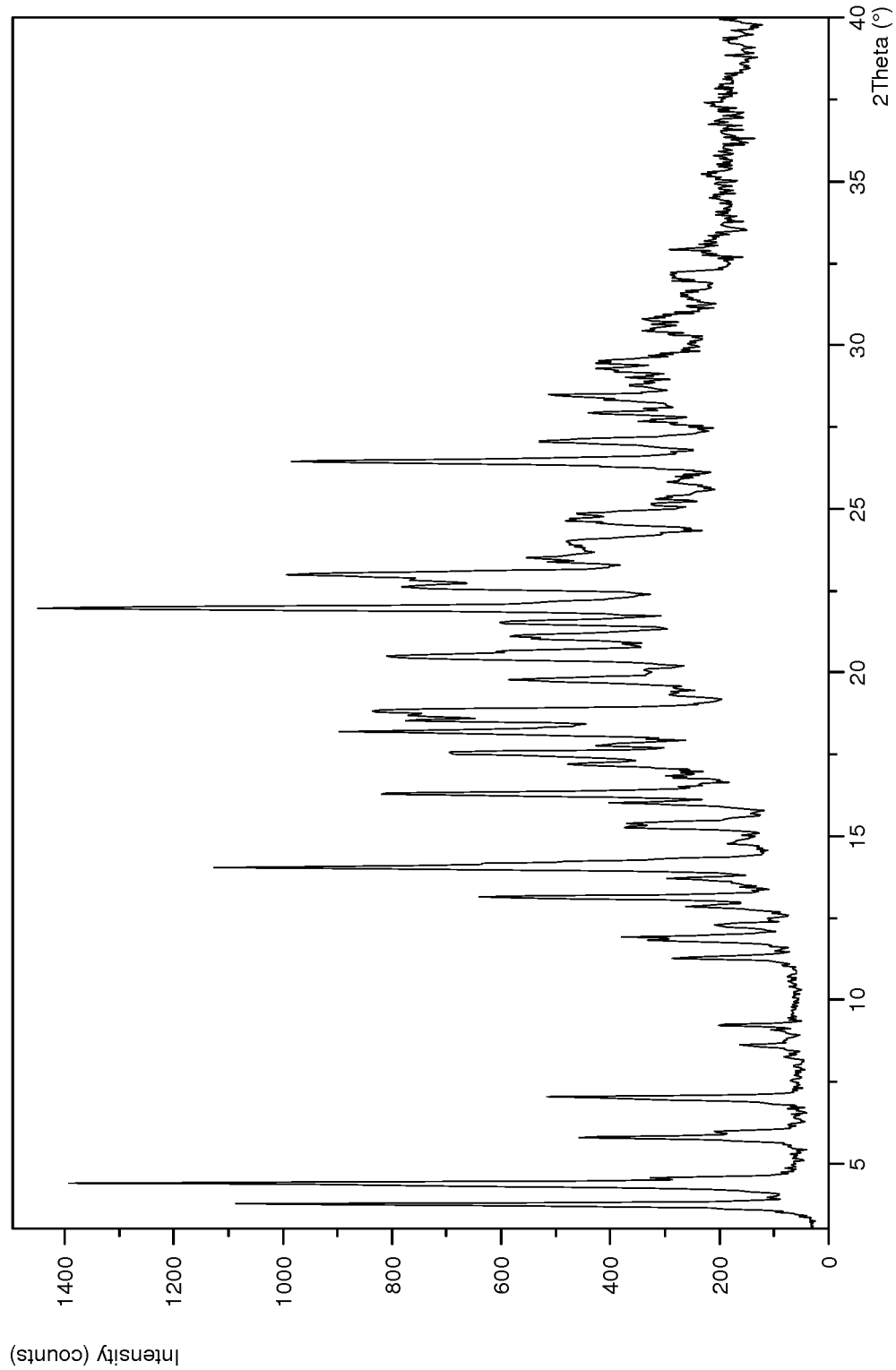

FIG. 3: XRPD diffractogram of the product obtained in Example 3. The x-axis shows the angle °2θ, and the y-axis the intensity in counts.

Figure 4A:
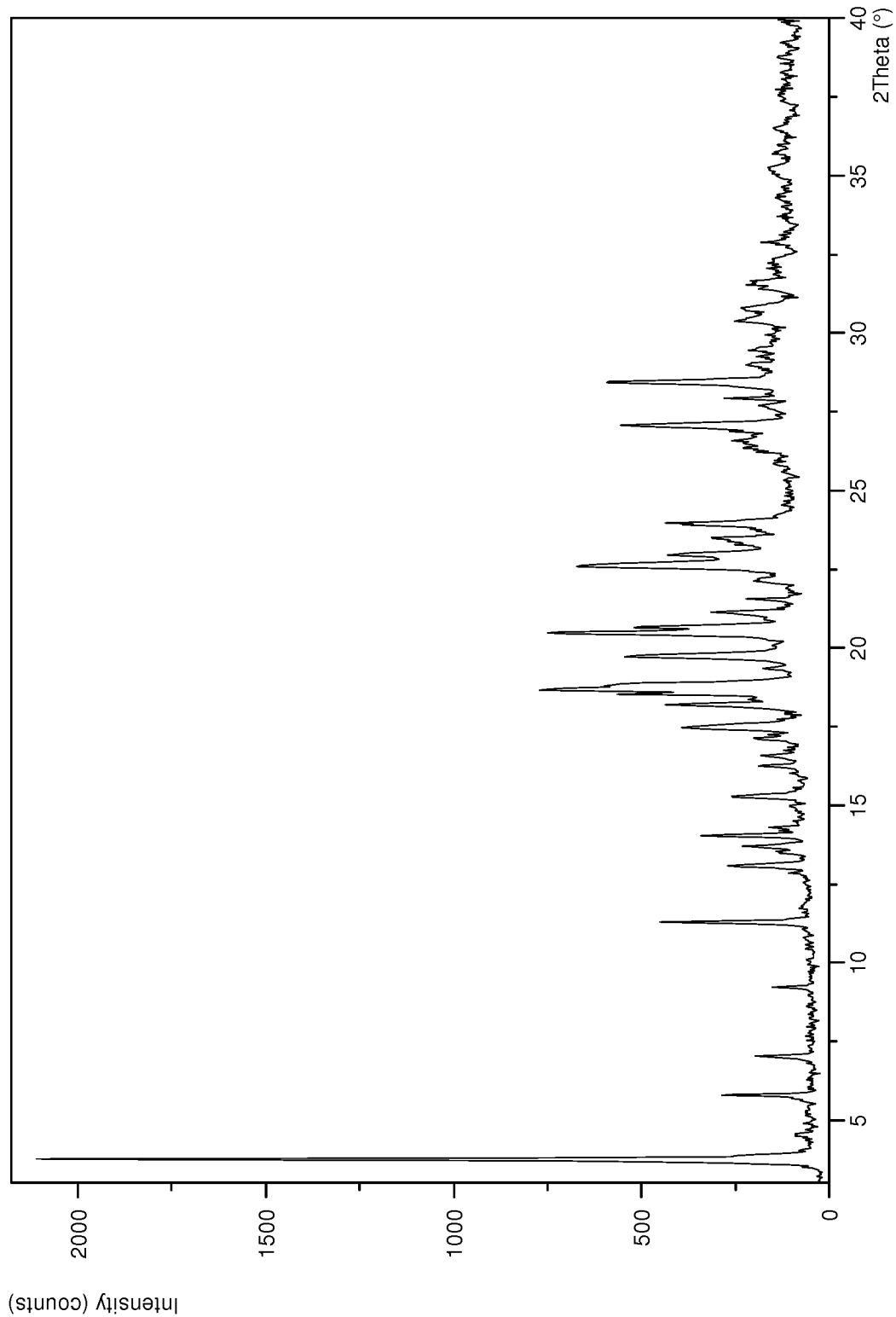

FIG. 4a: XRPD diffractogram of the product obtained in Example 4 after drying at RT overnight. The x-axis shows the angle °2θ, and the y-axis the intensity in counts.

Figure 4B:
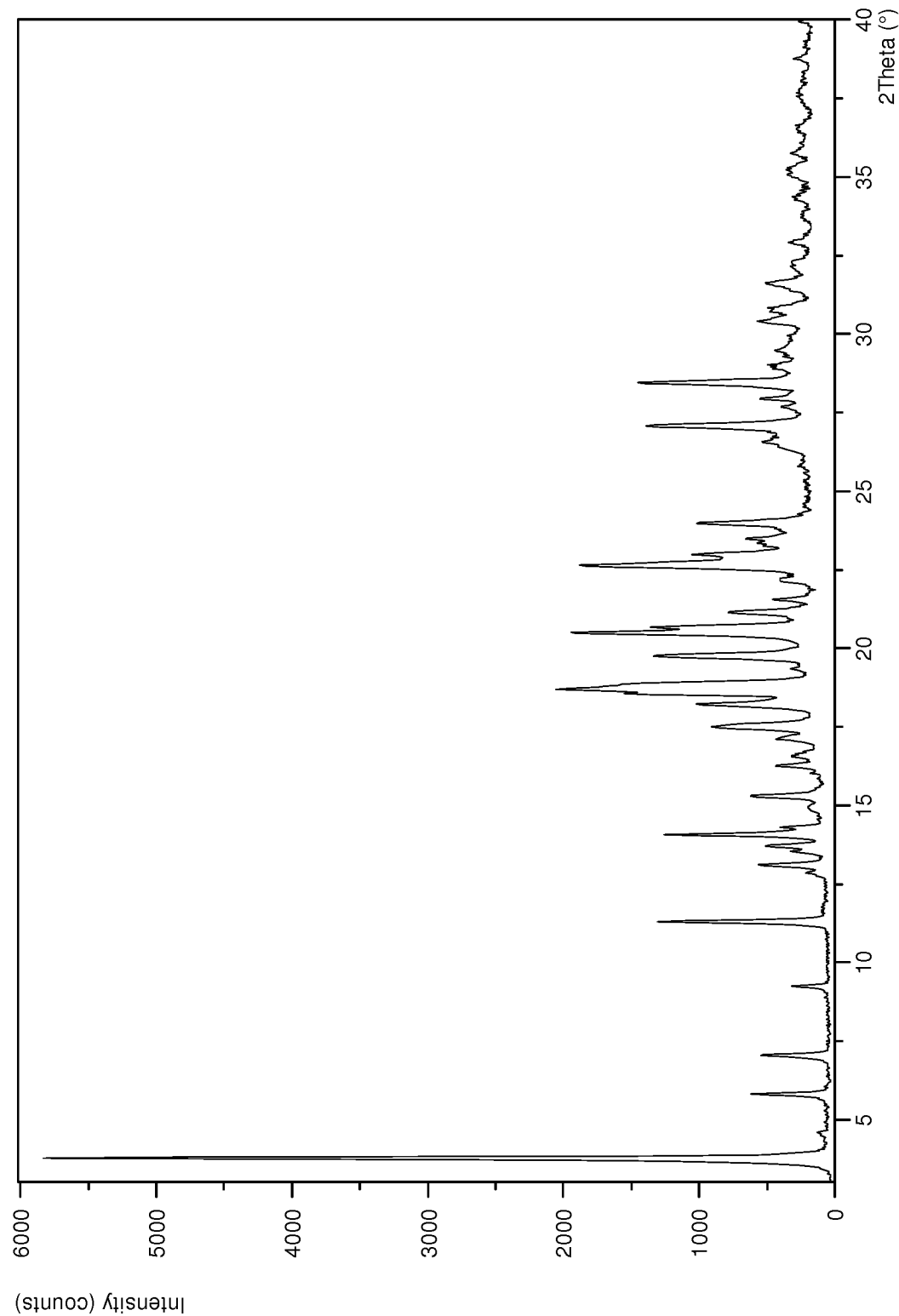

FIG. 4b: XRPD diffractogram of the product obtained in Example 4 after drying at 50° C. overnight. The x-axis shows the angle °2θ, and the y-axis the intensity in counts.

Figure 4C:
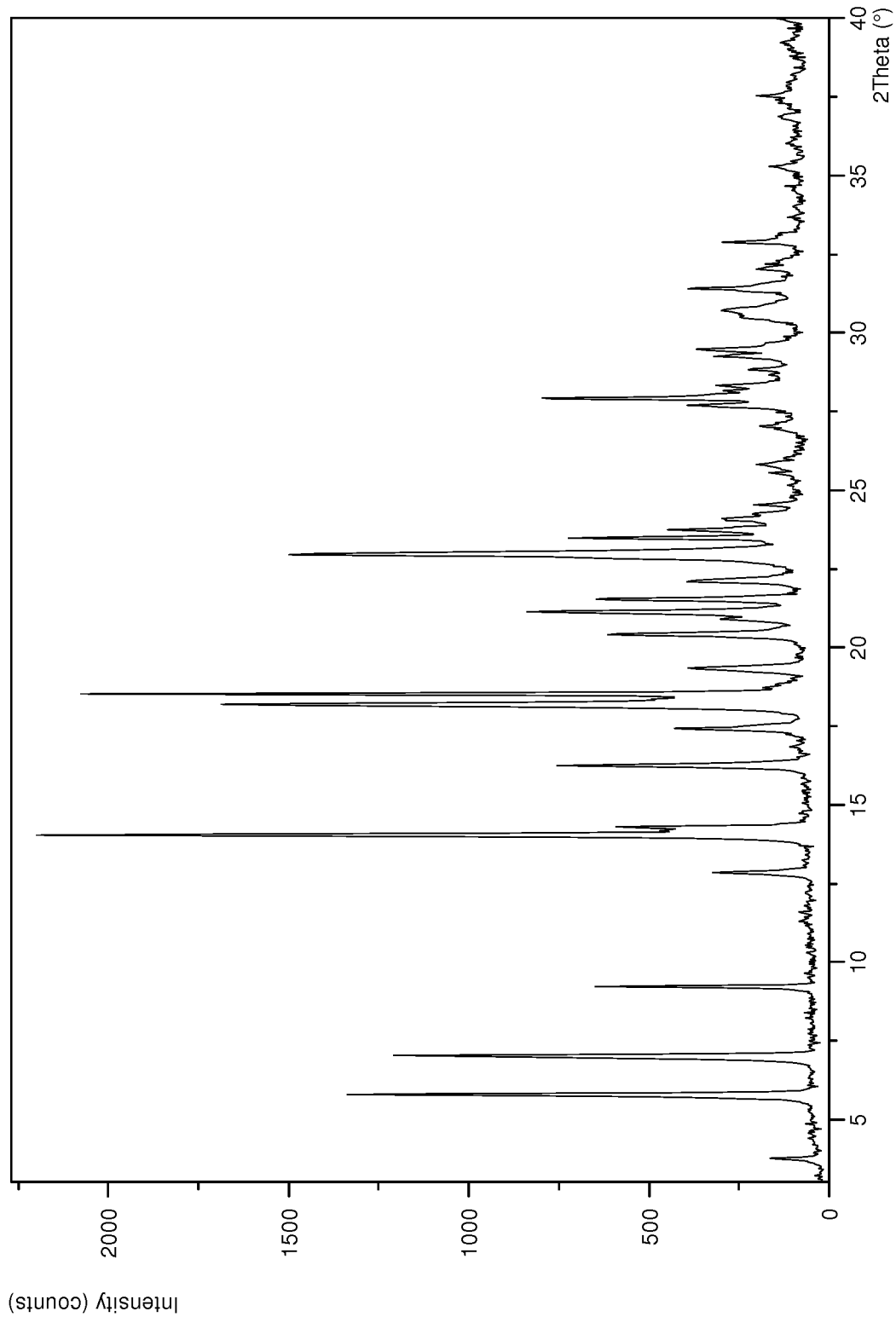

FIG. 4c: XRPD diffractogram of the product obtained in Example 4 after drying at 80° C. overnight. The x-axis shows the angle °2θ, and the y-axis the intensity in counts.

Figure 5:
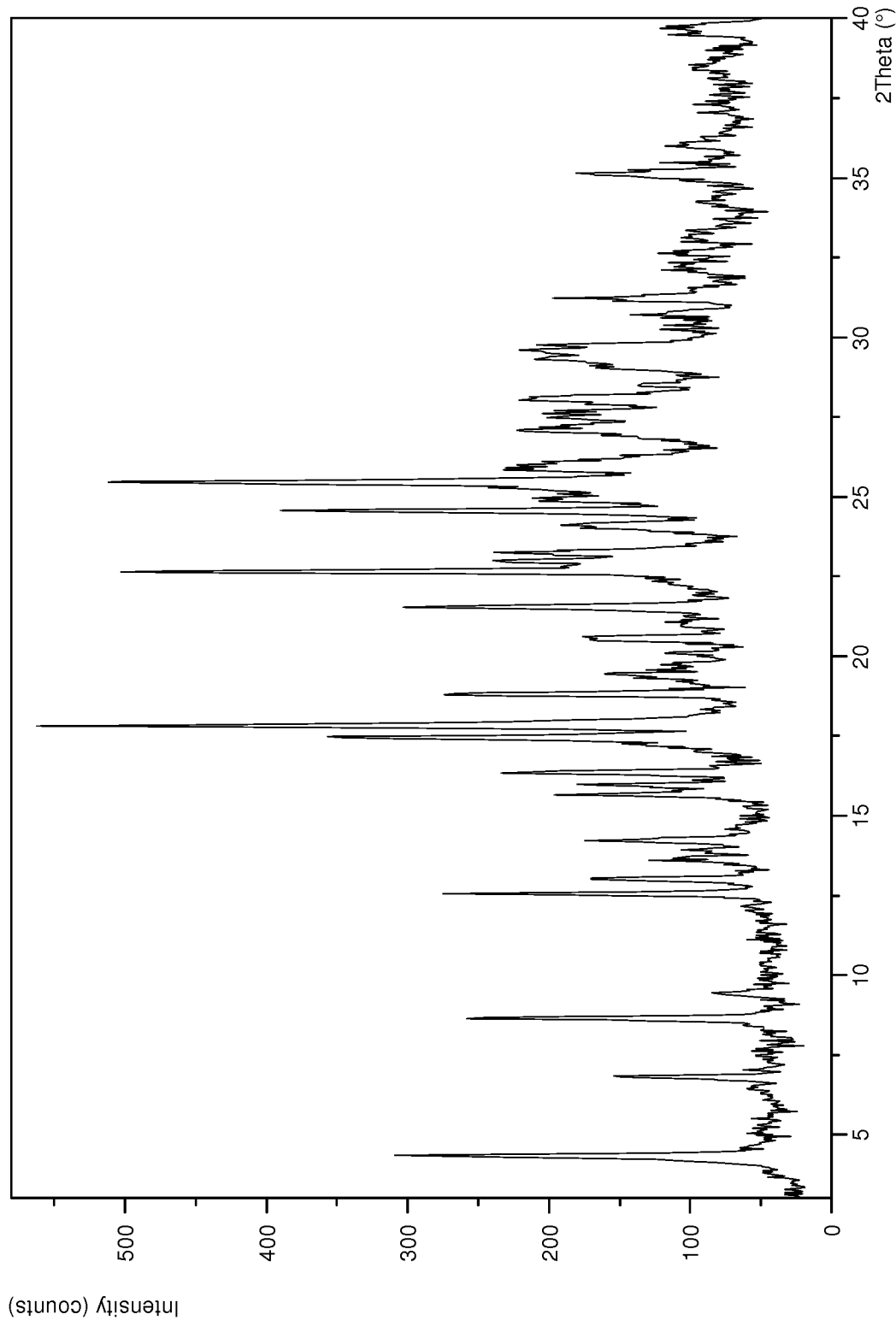

FIG. 5: XRPD diffractogram of the product obtained in Example 5. The x-axis shows the angle °2θ, and the y-axis the intensity in counts.

Figure 6A:
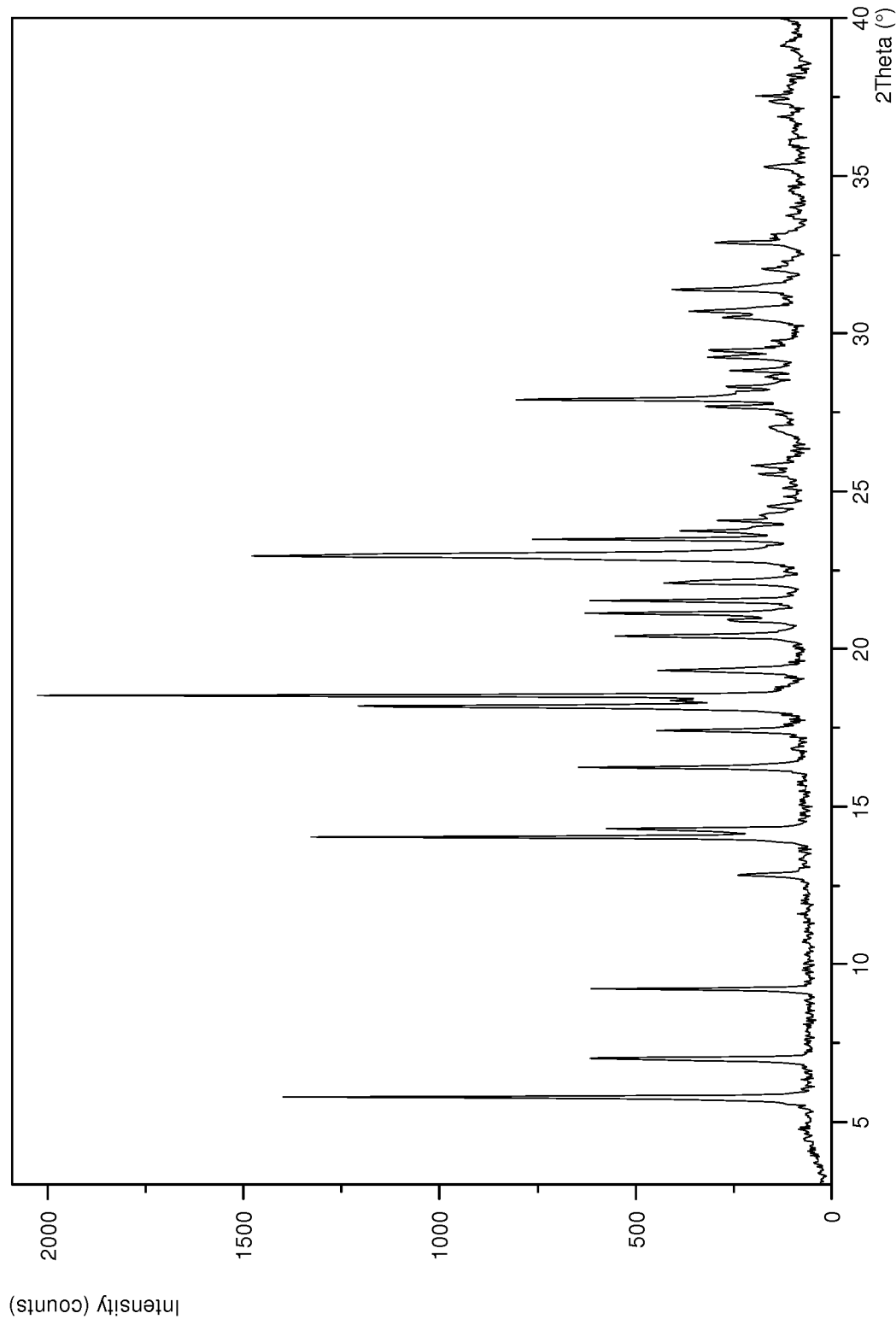

FIG. 6a: XRPD diffractogram of the product obtained in Example 6 after drying at RT overnight. The x-axis shows the angle °2θ, and the y-axis the intensity in counts.

Figure 6B:
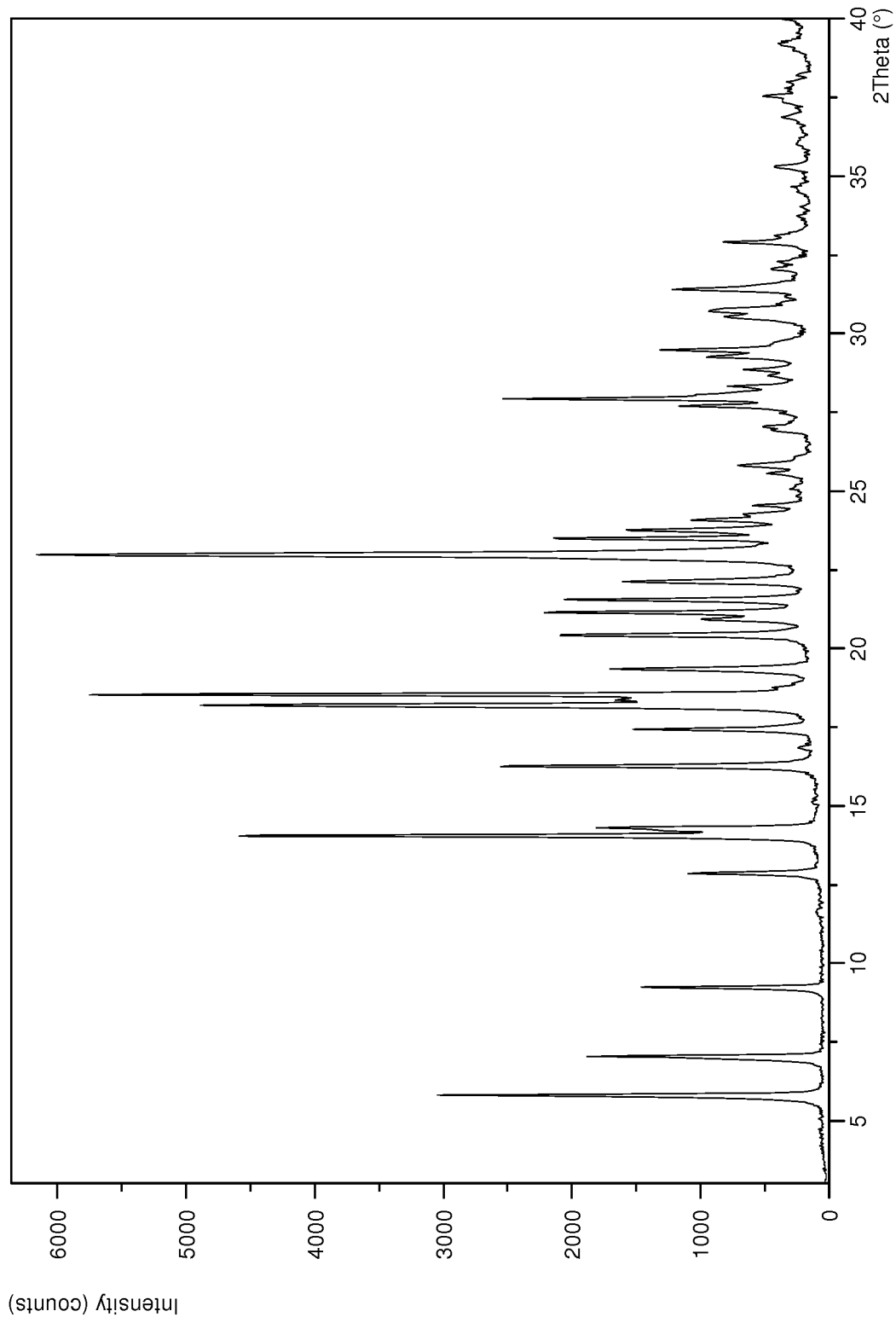

FIG. 6b: XRPD diffractogram of the product obtained in Example 6 after drying at 80° C. overnight. The x-axis shows the angle °2θ, and the y-axis the intensity in counts.

Figure 7:
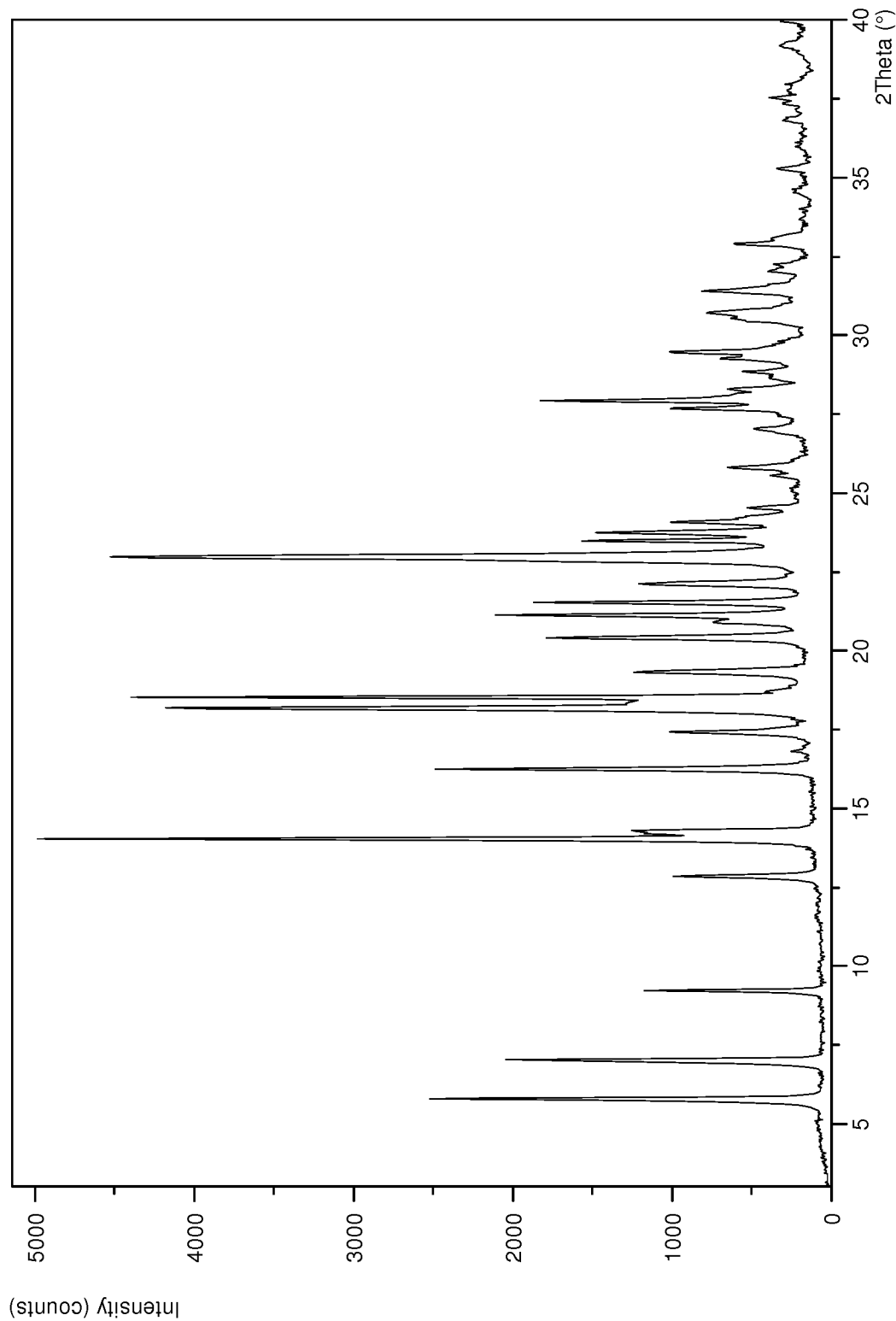

FIG. 7: XRPD diffractogram of the product obtained in Example 7. The x-axis shows the angle °2θ, and the y-axis the intensity in counts.

Figure 8:
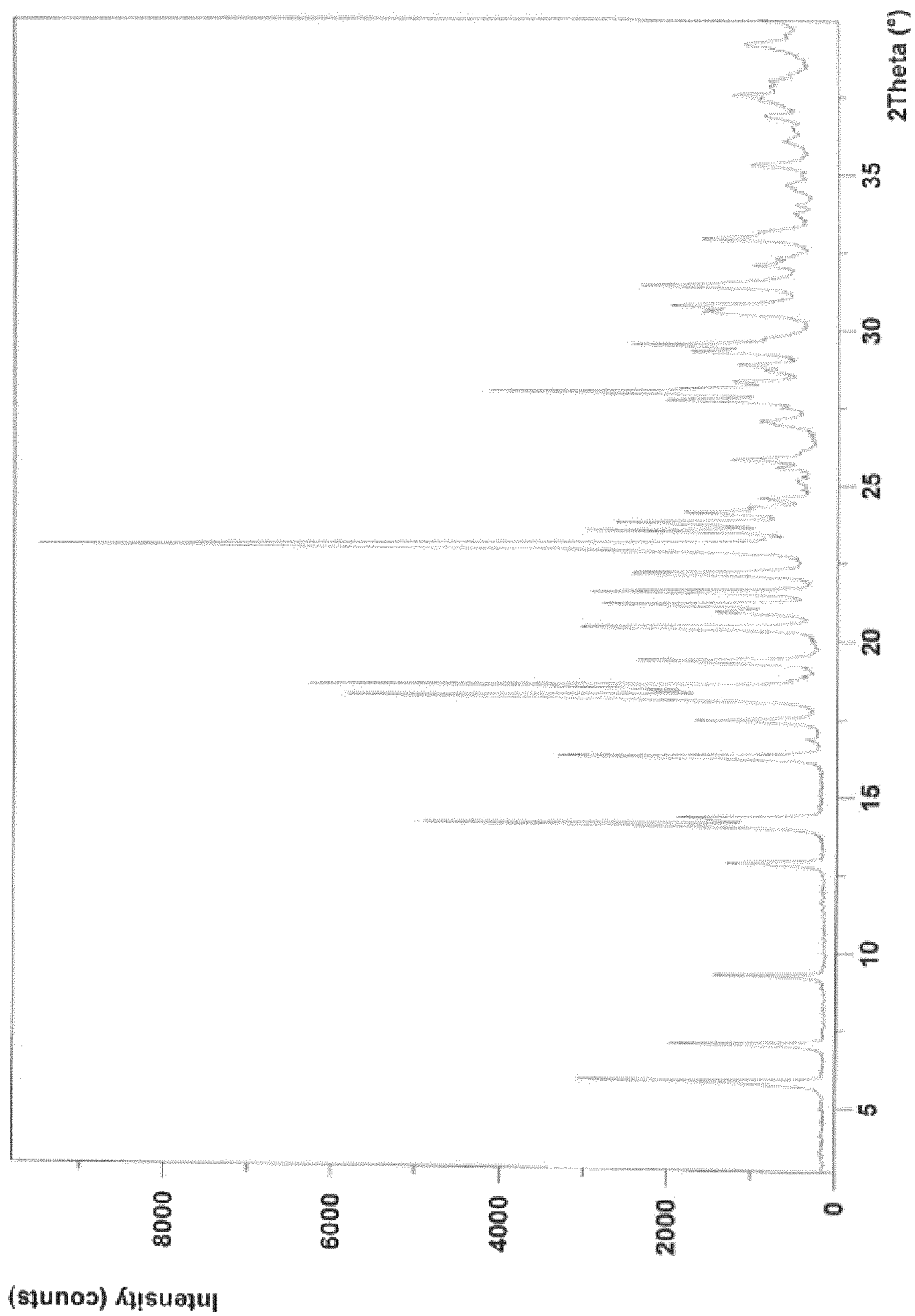

FIG. 8: XRPD diffractogram of the product obtained in Example 8. The x-axis shows the angle °2θ, and the y-axis the intensity in counts.

Figure 9:
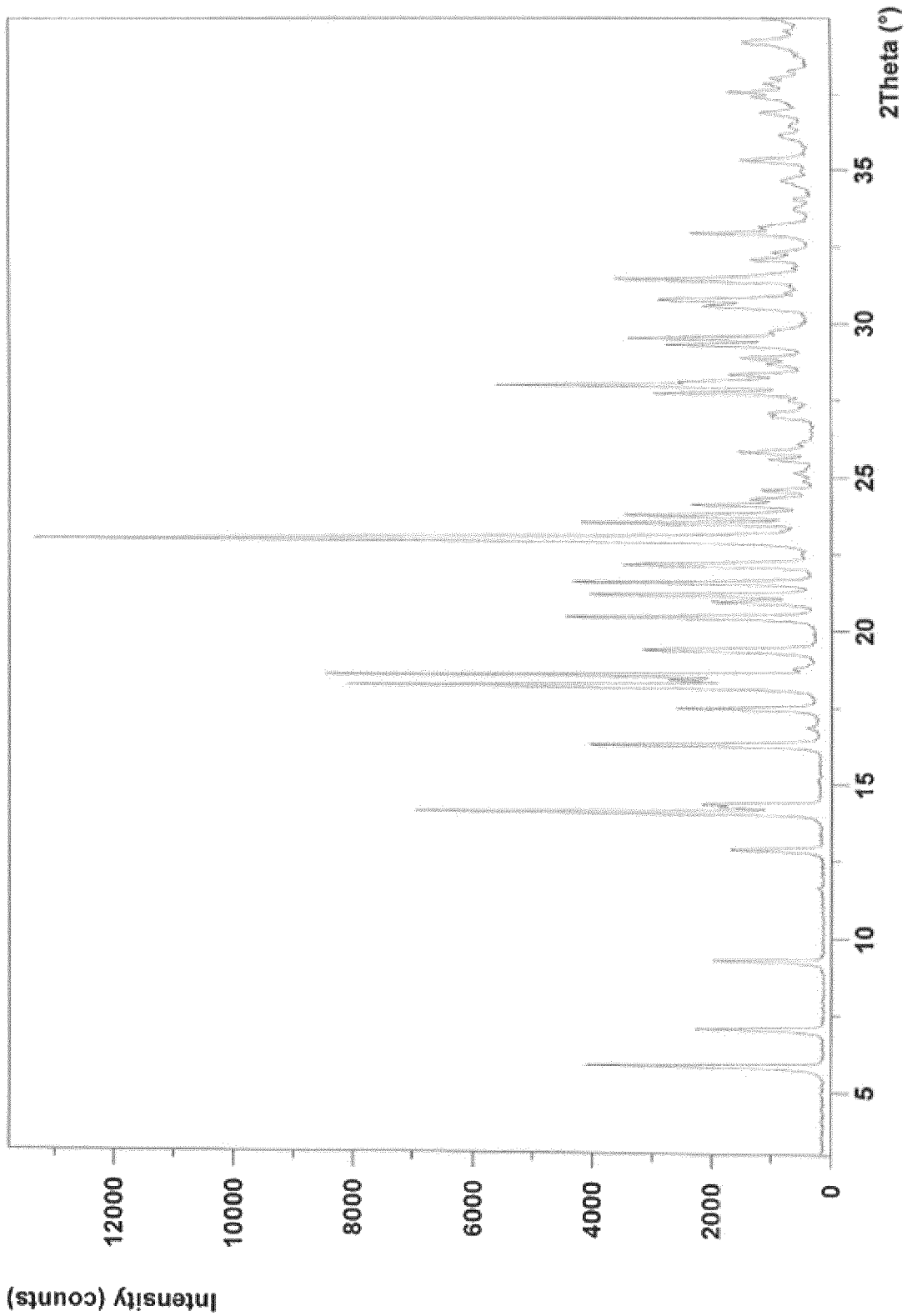

FIG. 9: XRPD diffractogram of the product obtained in Example 9. The x-axis shows the angle °2θ, and the y-axis the intensity in counts.

Figure 10:
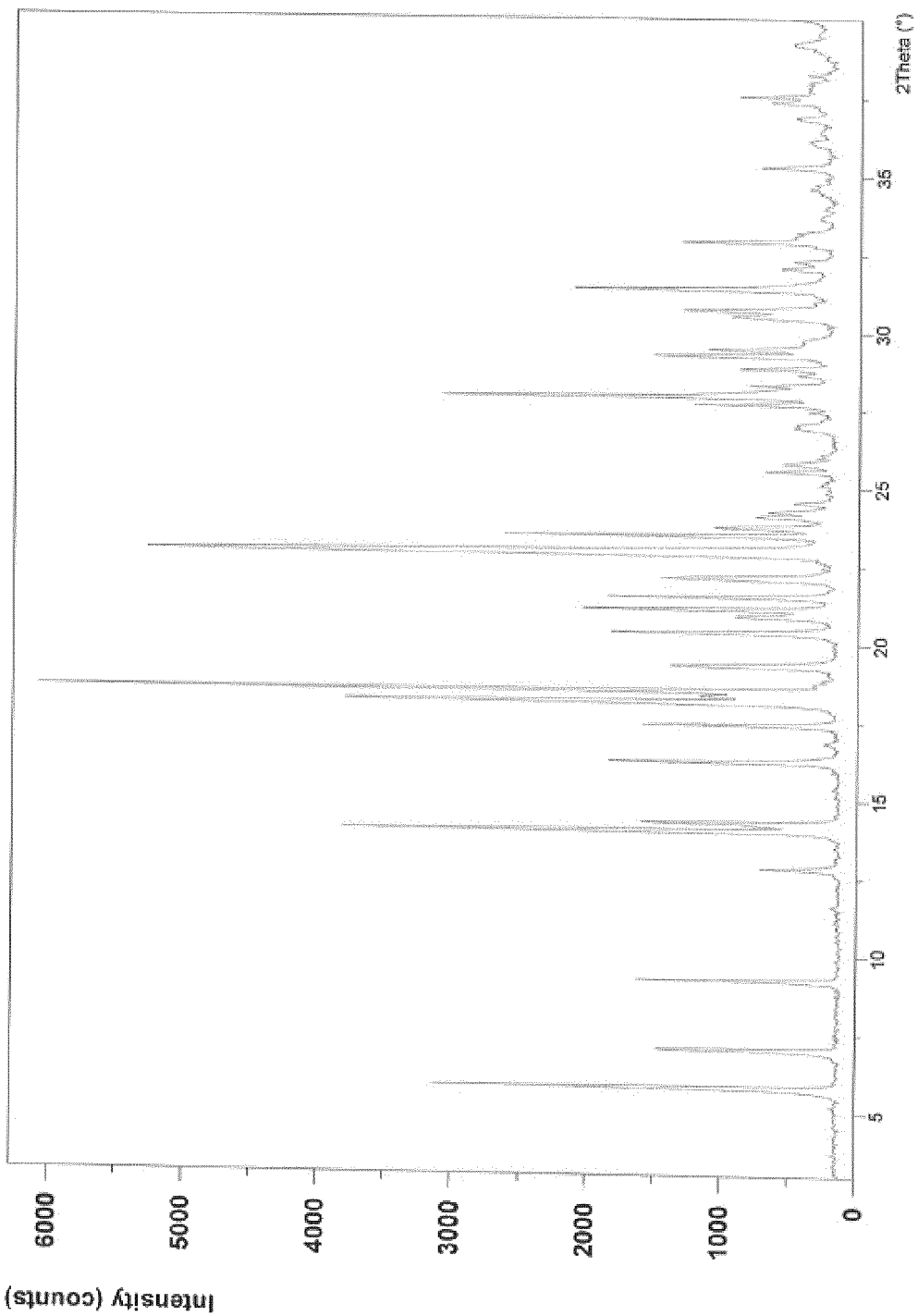

FIG. 10: XRPD diffractogram of the product obtained in Example 10. The x-axis shows the angle °2θ, and the y-axis the intensity in counts.

Figure 11:
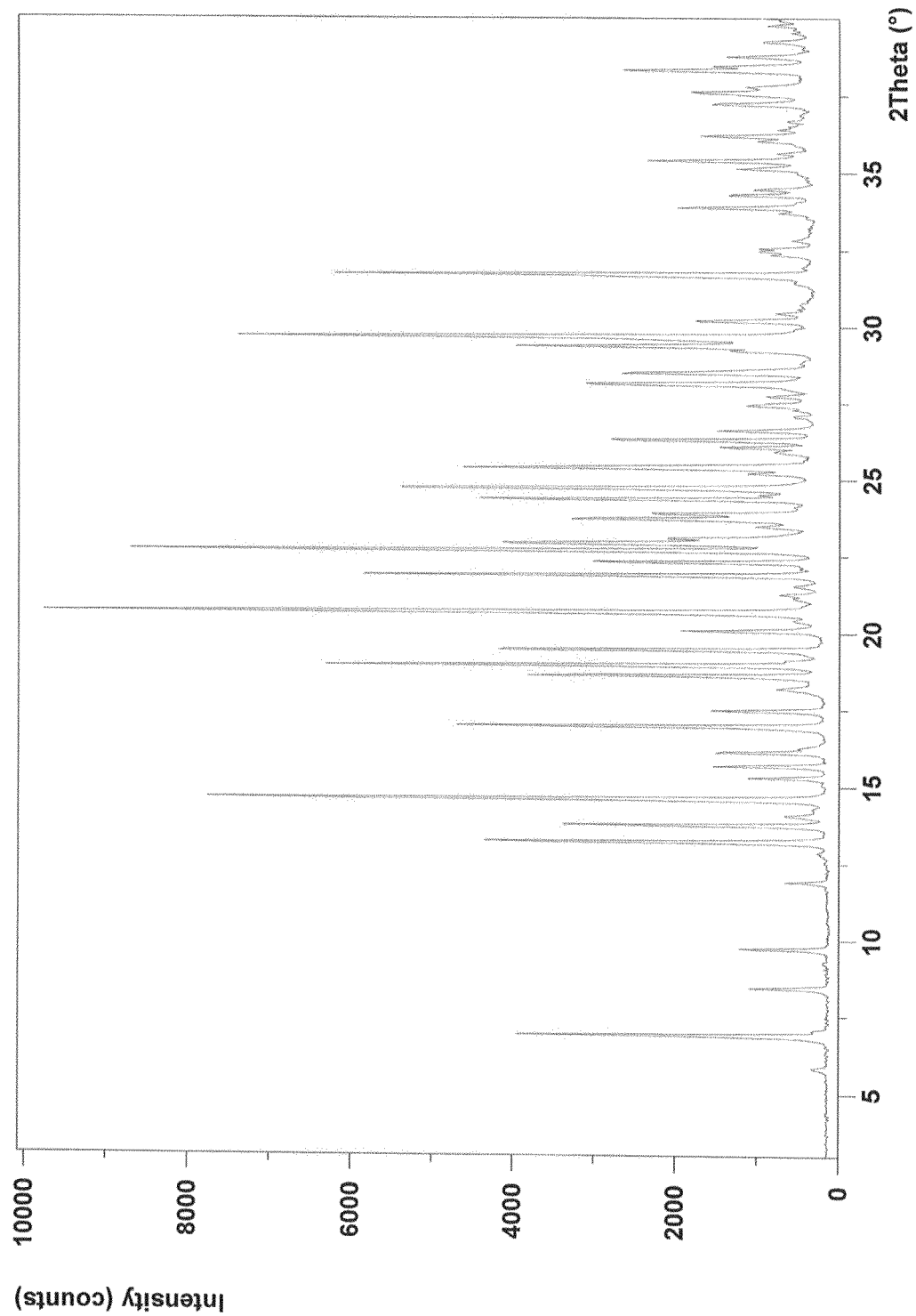

FIG. 11: XRPD diffractogram of the product obtained in Example 11. The x-axis shows the angle °2θ, and the y-axis the intensity in counts.

Figure 12:
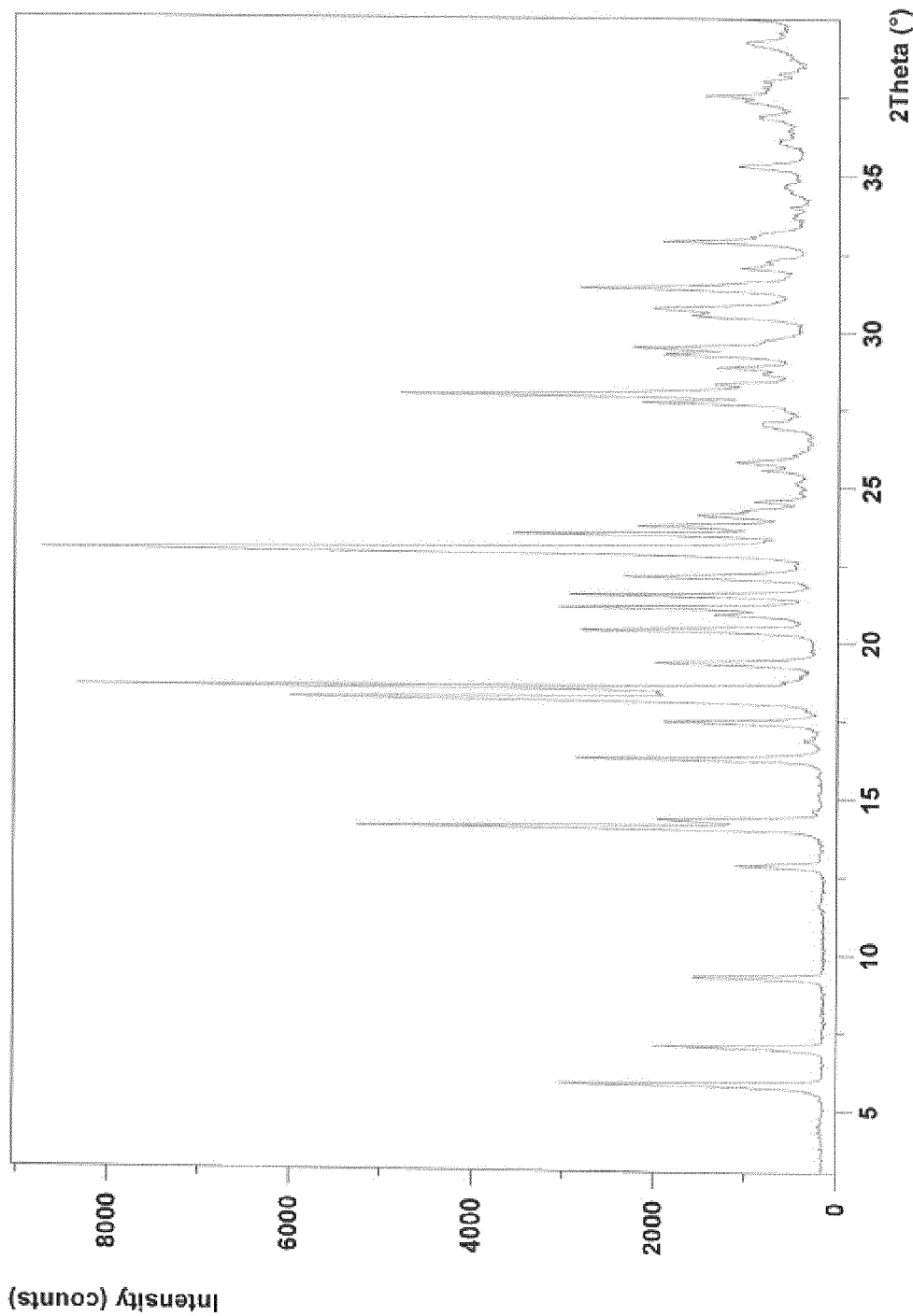

FIG. 12: XRPD diffractogram of the product obtained in Example 12. The x-axis shows the angle °2θ, and the y-axis the intensity in counts.

Figure 13:
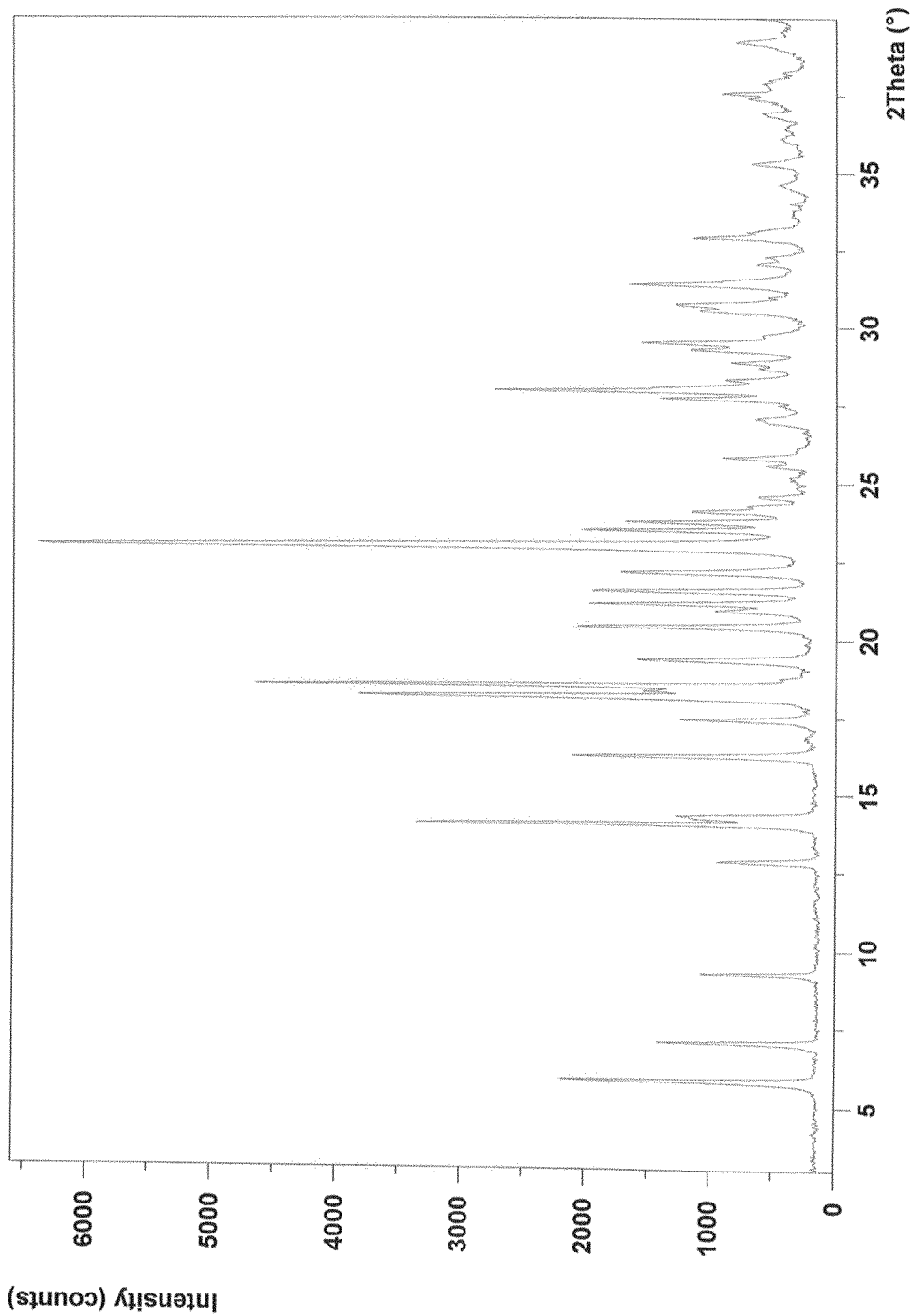

FIG. 13: XRPD diffractogram of the product obtained in Example 13. The x-axis shows the angle °2θ, and the y-axis the intensity in counts.

Figure 14:
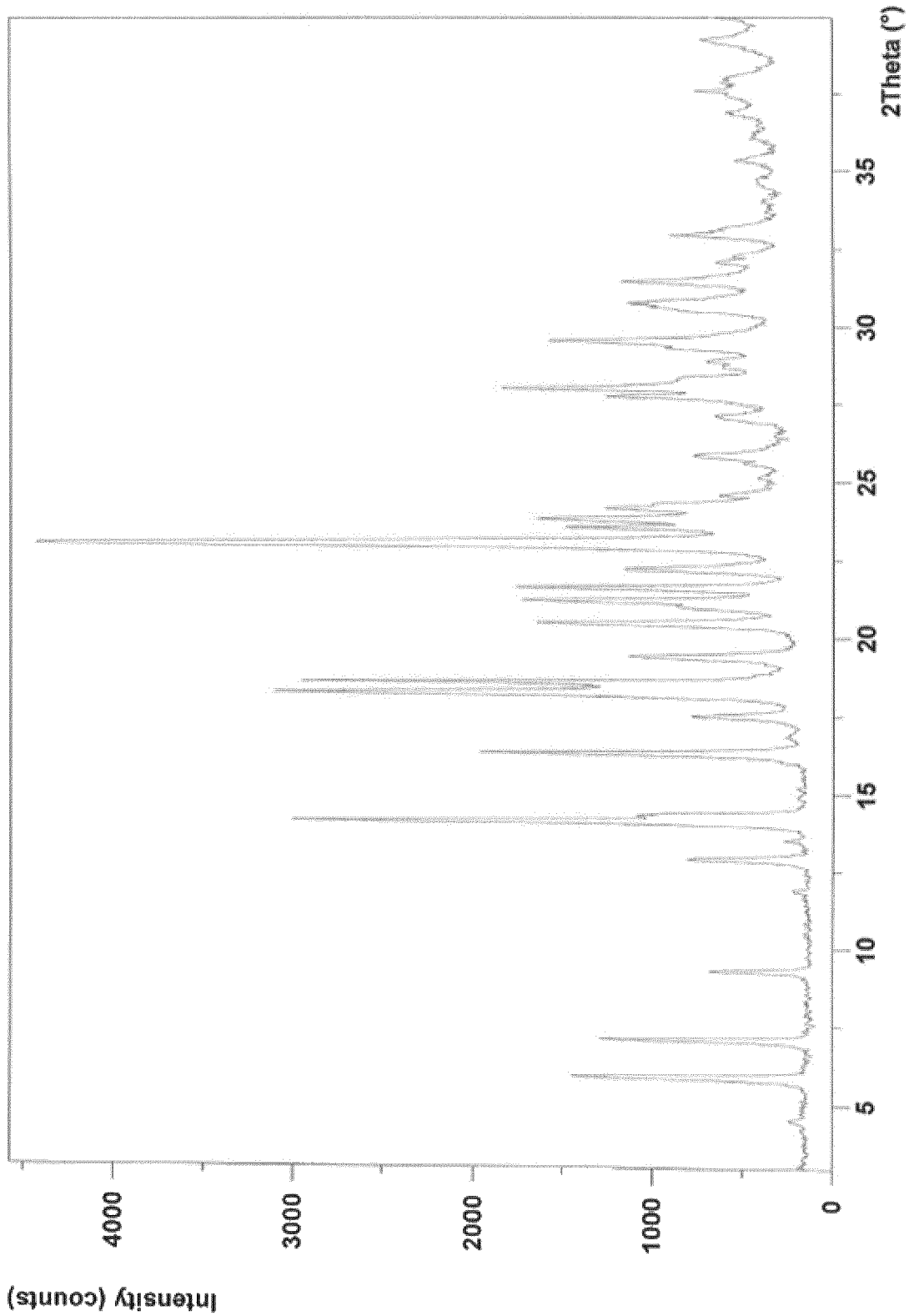

FIG. 14: XRPD diffractogram of the product obtained in Example 14. The x-axis shows the angle °2θ, and the y-axis the intensity in counts.

DETAILED DESCRIPTION OF THE INVENTION

The present invention provides a process for the manufacture of vortioxetine HBr α-form. This form is defined in WO 2007/144005, Examples 4a and 4b as crystalline vortioxetine HBr characterised by XRPD reflections at 5.85, 9.30, 17.49 and 18.58 (°2θ)(±0.1°). Similarly, vortioxetine HBr β-form is defined in WO 2007/144005, Examples 4c and 4d as crystalline vortioxetine HBr characterised by XRPD reflections at 6.89, 9.73, 13.78 and 14.62 (°2θ) (±0.1°). Similarly, vortioxetine HBr γ-form is defined in WO 2007/144005, Examples 4e and 4f as crystalline vortioxetine HBr characterised by XRPD reflections at 11.82, 16.01, 17.22 and 18.84 (°2θ)(±0.1°). The X-Ray powder diffractograms (XRPD) were measured on a PANalytical X'Pert PRO X-Ray Diffractometer using CuK$_{\alpha1}$ radiation. The samples were measured in reflection mode in the 2θ-range 5-40° using an X'celerator detector.

In the present context, "RT" is intended to indicate room temperature, i.e. a temperature between 19° C. and 25° C.

The solution obtained in step a) is vortioxetine free base in essentially pure toluene. In the present context, this may include a suspension of vortioxetine, i.e. a solution of vortioxetine with undissolved vortioxetine. For convenience both a solution where all vortioxetine is dissolved and a solution that also comprise undissolved vortioxetine will in the present context be referred to as a solution. Any indication of concentration or amount of vortioxetine will refer to the total amount of vortioxetine, i.e. the concentration or amount dissolved and undissolved vortioxetine.

In step a) of the present invention, a solution of vortioxetine in essentially pure toluene is obtained. In one embodiment, the concentration of vortioxetine in said solution is 10 g/l-500 g/l, such as 40 g/l-200 g/l, such as 50 g/l to 200 g/l, such as 50 g/l to 150 g/l, such as 100 g/l.

In step a) of the present invention, a solution of vortioxetine in essentially pure toluene is obtained. In one embodiment, "essentially pure" is intended to indicate that the toluene is more than 90% pure, such as more than 95% pure, such as more than 98% pure. The balance may include water (i.e. the application of not dry toluene) or other solvents or solvent impurities, such as benzene, xylenes, alkanes or alkenes. In the present context, "more than XX % pure" is intended to indicate that the solvent contains more than XX % toluene on weight/weight basis.

The temperature of the solution obtained in step a) is not believed to be critical but may influence how much vortioxetine can be brought into solution and how fast. In one embodiment, the temperature is between 0° C. and reflux temperature, such as between 5° C. and 50° C., such as between 10° C. and 30° C., such as around 20° C. In one embodiment, the temperature is between 25° C. and 40° C. That the temperature in step a) is said to be within a specified range, e.g. between 0° C. and reflux is intended to indicate that the temperature of the solution obtained in step a) at least at one point in time is within the specified range. In one embodiment, "at least at one point in time" is intended to indicate at least for 1 minute, such as at least for 5 minutes, such as at least for 10 minutes.

In step b) of the present invention the solution obtained in step a) is mixed with HBr and a $C_1$-$C_3$ carboxylic acid. The three components mixed in step b) (i.e. vortioxetine, HBr and $C_1$-$C_3$ carboxylic acid) may be mixed in any order. For instance, the solution obtained in step a) may be added to HBr and $C_1$-$C_3$ carboxylic acid, or HBr and $C_1$-$C_3$ carboxylic acid may be added to the solution obtained in step a).

The amount of HBr applied in step b) should be at least similar (on a molar basis) to that of vortioxetine in the solution obtained in step a) to optimize yield. If desired, the mixing in step b) may take place in more than one step wherein less than the full amount the solution obtained in step a) or the HBr and $C_1$-$C_3$ carboxylic acid is added in a single step. In one embodiment, the amount of HBr applied in step b) is between 0.9 and 10 mole equivalent relative to the amount of vortioxetine present in the solution obtained in step a), such as between 0.9 and 5 mole equivalent, such as 0.9 and 2 mole equivalent, such as between 0.9 and 1.3, such as between 0.9 and 1.1 mole equivalent relative to the amount of vortioxetine present in the solution obtained in step a).

The temperature in step b) is above 10° C. which is intended to indicate that the temperature when mixing the solution obtained in step a) and HBr and $C_1$-$C_3$ carboxylic acid to obtain mixture b) is above 10° C. In one embodiment, the temperature in step b) is 40° C. or below, such as at 25° C. or below.

After obtaining mixture b), the temperature may conveniently be lowered to decrease solubility and hence increase the yield of vortioxetine HBr α-form. In one embodiment, said temperature is between −20° C. and 30° C., such as between 0° C. and 20° C., such as between 0° C. and 10° C.

In one embodiment, the molar ratio HBr:$C_1$-$C_3$ carboxylic acid in step b) of the present invention is 1:1- to 1:10, such as 1:2-1:4, such as 1:2.9, or such as 1:7.7.

In the present context, $C_1$-$C_3$ carboxylic acid is intended to indicate formic acid, acetic acid or propionic acid, or a mixture thereof. In on embodiment, $C_1$-$C_3$ carboxylic acid is intended to indicate acetic acid, in which case, a 33% (w/w) HBr in acetic acid which is commercially available may conveniently be applied in step b). In one embodiment, $C_1$-$C_3$ carboxylic acid is intended to indicate propionic acid.

In one embodiment, the present invention provides a process for the manufacture of crystalline vortioxetine HBr α-form, the process comprising the steps of
  a) obtaining a solution of vortioxetine in essentially pure toluene, wherein said solution comprises 10 g/l-500 g/l vortioxetine, and wherein said essentially pure toluene comprises more than 90% (w/w) toluene, and wherein the temperature of said solution is between 5° C. and reflux;
b) mixing said solution obtained in step a) with HBr and $C_1$-$C_3$ carboxylic acid (such as acetic acid or propionic acid) to obtain mixture b), wherein the amount of HBr is 0.9-10 mole equivalent relative to the amount of vortioxetine in the solution obtained in step a), wherein the molar ratio of HBr:$C_1$-$C_3$ carboxylic acid is 1:1-1:10, and wherein the temperature of mixture b) is above 10° C.; and
c) collecting the precipitate obtained in step b).

In one embodiment, the present invention provides a process for the manufacture of crystalline vortioxetine HBr α-form, the process comprising the steps of
a) obtaining a solution of vortioxetine in essentially pure toluene, wherein said solution comprises 40 g/l-200 g/l, such as 50 g/l-200 g/l vortioxetine, and wherein said essentially pure toluene comprises more than 95% (w/w) toluene, and wherein the temperature of said solution is between 10° C. and 30° C., or between 25° C. and 40° C.;
b) mixing said solution obtained in step a) with HBr and $C_1$-$C_3$ carboxylic acid (such as acetic acid or propionic acid) to obtain mixture b), wherein the amount of HBr is 0.9-5 mole equivalent relative to the amount of vortioxetine in the solution obtained in step a), wherein the molar ratio of HBr:$C_1$-$C_3$ carboxylic acid is 1:1-1:8, such as 1:1-1:4, and wherein the temperature of mixture b) is above 10° C. and 40° C. or below, such as 25° C. or below; and
c) collecting the precipitate obtained in step b).

In one embodiment, the present invention provides a process for the manufacture of crystalline vortioxetine HBr α-form, the process comprising the steps of
a) obtaining a solution of vortioxetine in essentially pure toluene, wherein said solution comprises 40 g/l-200 g/l, such as 50 g/l-150 g/l vortioxetine, and wherein said essentially pure toluene comprises more than 98% (w/w) toluene, and wherein the temperature of said solution is between 20° C. and 25° C. or between 25° and 40° C.;
b) mixing said solution obtained in step a) with HBr and $C_1$-$C_3$ carboxylic acid (such as acetic acid or propionic acid) to obtain mixture b), wherein the amount of HBr is 0.9-1.3 mole equivalent relative to the amount of vortioxetine in the solution obtained in step a), wherein the molar ratio of HBr:$C_1$-$C_3$ carboxylic acid is 1:1-1:8, such as 1:1-1:4, or more specifically 1:3, and wherein the temperature of mixture b) is above 10° C. and below 40° C., such as below 25° C.; and
c) collecting the precipitate obtained in step b).

In one embodiment, the present invention provides a process for the manufacture of crystalline vortioxetine HBr α-form, the process comprising the steps of
a) obtaining a solution of vortioxetine in essentially pure toluene, wherein said solution comprises 100 g/l vortioxetine, and wherein said essentially pure toluene comprises more than 98% (w/w) toluene, and wherein the temperature of said solution is between 25° C. and 40° C., such as 20° C. and 25° C.;
b) mixing said solution obtained in step a) with HBr and $C_1$-$C_3$ carboxylic acid (such as acetic acid or propionic acid) to obtain mixture b), wherein the amount of HBr is 0.9-1.1 mole equivalent relative to the amount of vortioxetine in the solution obtained in step a), wherein the molar ratio of HBr:$C_1$-$C_3$ carboxylic acid is 1:1-1:3, and wherein the temperature of mixture b) is above 10° C. and 40° C. or below, such as 25° C. or below; and
c) collecting the precipitate obtained in step b).

The experiments reported in Reference Examples 1-5, 11 and 14 show that precipitation of vortioxetine HBr from toluene over a range of conditions fails to provide the desired α-form. A range of vortioxetine concentrations have been investigated (50 g/l-160 g/l), variations in solvent has been investigated (pure toluene and 95% toluene in water), and different temperatures have also been investigated (−15° C.-50° C.). Finally, use of pre-formed vortioxetine HBr as well as vortioxetine HBr formation by addition of liquid and gaseous HBr has been investigated. In addition to the conclusion that the investigated process conditions appear unable to provide the desired α-form, the results from examples 1-5 also show that seemingly small variations in process conditions give rise to differences in the crystal form precipitated.

Contrary hereto, the experiments shown in Examples 6-10, 12 and 13 define process conditions which give the desired vortioxetine HBr α-form in a robust and high-yielding process.

In one embodiment the invention provides crystalline vortioxetine HBr α-form as obtained by a process of the present invention.

In one embodiment the invention provides a pharmaceutical composition comprising crystalline vortioxetine HBr α-form as obtained by a process of the present invention and a pharmaceutically acceptable excipient.

EXPERIMENTS

X-Ray powder diffractograms (XRPD) were measured on a PANalytical X'Pert PRO X-Ray Diffractometer using CuKα1 radiation (λ=1.5406 Å). The samples were measured in reflection mode in the 2θ-range 3-40° using an X'celerator detector.

Example 1 (Reference)

To a 2 L three necked flask equipped with mechanical stirring, a thermometer and a reflux condenser was added toluene (600 mL) and vortioxetine (100 g, 0.335 mol). The mixture was heated with a heating mantle to 65° C. and water (27 mL, 1.5 mol) was added to obtain a clear solution. The heating mantle was removed and aqueous HBr (48%, 39.8 mL (59.3 g), 0.352 mol) was added. The flask was cooled immediately on ice/water. After few minutes at a temperature of 50-55° C. precipitation started. Stirring was continued and the mixture was allowed to cool to 5° C. over the next 20 min. Stirring was continued for further 20 min. The precipitated product was isolated by filtration, washed on the filter with toluene (3×40 mL) and dried in vacuo at 40° C. over-night. Yield 126.0 g. NMR showed presence of very little toluene. XRPD showed that the isolated product was a mixture of vortioxetine HBr α-form and β-form. The XRPD obtained is shown in FIG. 1.

Example 2 (Reference)

Vortioxetine HBr (1.0 gram, 2.64 mmol) was attempted dissolved in toluene (6.0 mL) and water (0.27 mL) by heating the mixture to reflux for 5 minutes; however a clear solution was not obtained. More toluene (12 mL) and water was added (0.54 mL). The clear mixture was crash-cooled on an ice/NaCl mixture and stirred for 30 min. The precipitate was isolated by filtration and washed with toluene (3×1 mL) on the filter and dried in vacuo at room temperature overnight. Yield: 1.1 gram. XRPD showed that pure vortioxetine HBr 3-form was obtained. The XRPD obtained is shown in FIG. 2.

Example 3 (Reference)

Vortioxetine (1.0 gram, 3.35 mmol) was dissolved in toluene (6.0 mL) and water (0.27 mL) by heating the mixture to 65° C. Aqueous HBr (48%, 0.4 mL (0.59 g), 3.52 mmol) was added and the mixture was crash-cooled on an ice/NaCl mixture (to −15° C.) over 10 minutes and stirred for an additional 30 min. The precipitate was isolated by filtration and washed with toluene (3×2 mL) on the filter and dried in vacuo at room temperature overnight. Yield: 1.16 gram. XRPD showed that the product obtained was a mixture of vortioxetine HBr α-form, vortioxetine HBr hydrate and an unidentified component. Moreover, XRPD indicated a low degree of crystallinity. The XRPD obtained is shown in FIG. 3.

Example 4 (Reference)

To a 500 mL three necked flask equipped with mechanical stirring, a thermometer and a reflux condenser was added toluene (200 mL) and vortioxetine (20.0 g, 67.0 mmol). The mixture was stirred at RT overnight to obtain a clear solution. Aqueous HBr (48%, 7.96 mL (11.9 g), 70.4 mmol) was added quickly and the reaction mixture was cooled on an ice/water bath immediately after. Stirring was continued in the cold for 10 minutes. The precipitated product was isolated by filtration, washed on the filter with toluene (2×30 mL) and dried in vacuo at RT, 50° C. and 80° C. overnight. Yield 24.57 g. NMR showed no presence of toluene. XRPD showed that the product obtained after drying the precipitate at RT and 50° C. overnight is a mixture of vortioxetine HBr α-form and a vortioxetine HBr hydrate, and that drying at 80° C. overnight reduces the amount of vortioxetine HBr hydrate, probably by removing the crystal water. The XRPD obtained after drying at RT, 50° C. and 80° C. are shown in FIGS. 4a, 4b and 4c, respectively.

Example 5 (Reference)

To a 250 mL three necked flask equipped with magnetic stirring, a thermometer and a reflux condenser was added toluene (80 mL) and vortioxetine (4.0 g, 13.4 mmol). The mixture was stirred to obtain a clear solution. Hydrogen bromide (gas) (approx. 1.1 g, 13.5 mmol) was added carefully from a lecture bottle. A precipitate started to form immediately and after measurement of the pH (approx. pH=1) stirring was continued at RT for one hour. The precipitated product was isolated by filtration, washed on the filter with toluene (2×10 mL). The product filtered very slowly and was dried in vacuo at 40° C. to constant weight. Yield 5.97 g. XRPD showed that the isolated product could not be identified as vortioxetine HBr α-form. NMR also revealed that the product obtained contained significant amounts of toluene. TGA showed a loss of approx. 13% weight between 50-110° C. Continued drying at 130° C. decomposed the isolated product into a brown to black material. The XRPD obtained is shown in FIG. 5.

Example 6

To a 500 mL three necked flask equipped with mechanical stirring, a thermometer and a reflux condenser was added toluene (200 mL) and vortioxetine (20.0 g, 67.0 mmol). The mixture was stirred at RT for 30 minutes to obtain a clear solution. HBr in acetic acid (33%, 12.32 mL (17.25 g), 70.4 mmol) was added quickly and the reaction mixture was cooled on an ice/water bath immediately thereafter. Stirring was continued cold for 10 minutes. The precipitated product was isolated by filtration, washed on the filter with toluene (2×30 mL) and dried in vacuo at RT and 80° C. overnight. Yield 23.77 g. XRPD showed that the isolated product was pure vortioxetine HBr α-form, irrespective of drying conditions. The XRPD obtained after drying at RT and 80° C. are shown in FIGS. 6a and 6b, respectively.

Example 7

To a 4 L three necked flask equipped with mechanical stirring, a thermometer and a reflux condenser was added toluene (3000 mL) and vortioxetine (300 g, 1.005 mol). The mixture was stirred at RT for 30 minutes to obtain a clear solution. The clear solution was cooled to 10° C. HBr in acetic acid (33%, 185 mL (259 g), 1.055 mol) was added from a pressure-equalizing funnel over 5 min. The addition caused the temperature to rise to 23° C. Precipitation started shortly after the first few mLs of the HBr in acetic acid mixture had been added and was rather heavy until approx. half of the HBr in acetic acid mixture had been added. At this point most of the precipitate re-dissolved and during the continued addition of HBr in acetic acid mixture precipitation started again. Stirring was continued for 45 min while the temperature was lowered to 5° C. The precipitate was isolated by filtration, washed on the filter with toluene (3×100 mL) and dried in vacuo at RT overnight. Yield 375.4 g. XRPD showed that the isolated product was pure vortioxetine HBr α-form. The XRPR obtained is shown in FIG. 7.

Example 8

To a 100 ml flask equipped with magnetic stirring was added toluene (50 ml) and vortioxetine (2.0 g, 6.7 mmol). The mixture was stirred at RT for 30 minutes. HBr in acetic acid (33%, 1.23 ml, 1.73 g, 7.04 mmol) was added quickly and the reaction mixture was cooled on an ice/water bath immediately thereafter. Stirring continued for 10 minutes. The precipitated product was isolated by filtration, washed on the filter with toluene (2×5 ml) and dried in vacuo at RT overnight. Yield 2.41 g. XRPD showed that the isolated product was pure vortioxetine HBr α-form. The XRPR obtained is shown in FIG. 8.

Example 9

To a 50 ml flask equipped with magnetic stirring was added toluene (10 ml) and vortioxetine (2.0 g, 6.7 mmol). The mixture was stirred at RT for 30 minutes. To obtain a clear solution the temperature was increased to 40° C. HBr in acetic acid (33%, 1.23 ml, 1.73 g, 7.04 mmol) was added quickly and the reaction mixture was cooled on an ice/water bath immediately thereafter. Stirring continued for 2 minutes after which additional toluene was added (5.5 ml) to allow continued stirring (10 minutes). The precipitated product was isolated by filtration, washed on the filter with toluene (2×5 ml) and dried in vacuo at RT overnight. Yield 2.44 g. XRPD showed that the isolated product was pure vortioxetine HBr α-form. The XRPR obtained is shown in FIG. 9.

Example 10

To a 50 ml flask equipped with magnetic stirring was added toluene (20 ml) and vortioxetine (2.0 g, 6.7 mmol). The mixture was stirred at 40° C. for 30 minutes. HBr in acetic acid (33%, 1.23 ml, 1.73 g, 7.04 mmol) was added quickly and the reaction mixture was cooled on an ice/water bath immediately thereafter. Stirring was obstructed by precipitation and additional toluene was added (5.5 ml) to allow continued stirring (10 minutes). The precipitated product was isolated by filtration, washed on the filter with toluene (2×5 ml) and dried in vacuo at RT overnight. Yield 2.30 g. XRPD showed that the isolated product was pure vortioxetine HBr α-form. The XRPR obtained is shown in FIG. 10.

Example 11 (Reference)

To a 50 ml flask equipped with magnetic stirring was added toluene (10 ml) and vortioxetine (2.0 g, 6.7 mmol). The mixture was stirred at RT for 10 minutes followed by stirring at 10° C. for 10 minutes. HBr in acetic acid (33%, 1.23 ml, 1.73 g, 7.04 mmol) was added quickly and the reaction mixture was cooled on an ice/water bath immediately thereafter. Stirring continued for 10 minutes. The precipitated product was isolated by filtration, washed on the filter with toluene (2×5 ml) and dried in vacuo at RT overnight. Yield 2.43 g. XRPD showed that the isolated product was pure vortioxetine HBr β-form. The XRPR obtained is shown in FIG. 11.

Example 12

To a 50 ml flask equipped with magnetic stirring was added toluene (20 ml) and vortioxetine (2.0 g, 6.7 mmol). The mixture was stirred at RT for 30 minutes. Acetic acid (2.00 ml, 2.10 g, 34.9 mmol) and HBr in acetic acid (33%, 1.23 ml, 1.73 g, 7.04 mmol) was added quickly and the reaction mixture was stirred for 20 minutes following which it was cooled on an ice/water bath. Stirring was obstructed by precipitation and additional toluene was added (5.5 ml) to allow continued stirring (10 minutes). The precipitated product was isolated by filtration, washed on the filter with toluene (2×5 ml) and dried in vacuo at RT overnight. Yield 2.15 g. XRPD showed that the isolated product was pure vortioxetine HBr α-form. The XRPR obtained is shown in FIG. 12.

Example 13

To a 50 ml flask equipped with magnetic stirring was added toluene (20 ml) and vortioxetine (2.0 g, 6.7 mmol). The mixture was stirred at RT for 30 minutes. HBr in propionic acid (33%, 1.23 ml, 1.73 g, 7.04 mmol) was added quickly and the reaction mixture was cooled on an ice/water bath. The HBr in propionic aid solution was obtained by bubbling HBr gas through propionic acid until the desired weight increase was obtained. Stirring continued for 20 minutes. The precipitated product was isolated by filtration, washed on the filter with toluene (2×5 ml) and dried in vacuo at RT for four days. Yield 1.91 g. XRPD showed that the isolated product was pure vortioxetine HBr α-form. The XRPR obtained is shown in FIG. 13.

Example 14 (Reference)

To a 50 ml flask equipped with magnetic stirring was added toluene (20 ml) and vortioxetine (2.0 g, 6.7 mmol). The mixture was stirred at RT for 10 minutes followed by stirring at 10° C. for additional 10 minutes. HBr in acetic acid (33%, 1.23 ml, 1.73 g, 7.04 mmol) was added quickly following which the reaction mixture was cooled on an ice/water bath and stirring continued for 10 minutes. The precipitated product was isolated by filtration, washed on the filter with toluene (2×5 ml) and dried in vacuo at RT overnight. Yield 2.46 g. XRPD showed that the isolated product was vortioxetine HBr α-form also containing vortioxetine HBr γ-form. The XRPR obtained is shown in FIG. 14.

The invention claimed is:

1. A process for the manufacture of crystalline vortioxetine HBr α-form, the process comprising the steps of
   a) obtaining a solution of vortioxetine in essentially pure toluene;
   b) mixing said solution obtained in step a) with HBr and $C_1$-$C_3$ carboxylic acid to obtain mixture b) at a temperature above 10° C.; and
   c) collecting the precipitate obtained in step b).

2. The process according to claim 1, wherein the concentration of vortioxetine obtained in step a) is between 10 g/l toluene and 500 g/l toluene.

3. The process according to claim 1, wherein the concentration of vortioxetine obtained in step a) is between 40 g/l toluene and 200 g/l toluene.

4. The process according to claim 1, wherein said essentially pure toluene contains more than 95 (w/v) % toluene.

5. The process according to claim 1, wherein the temperature of the solution obtained in step a) is between 0° C. and reflux.

6. The process according to claim 1, wherein the temperature of the solution obtained in step a) is between 25° C. and 40° C.

7. The process according to claim 1, wherein the amount of HBr in step b) is between 0.9 and 2 mole equivalent relative to the amount of vortioxetine present in the solution obtained in step a).

8. The process according to claim 1, wherein the amount of HBr in step b) is between 1 and 1.3 mole equivalent relative to the amount of vortioxetine present in the solution obtained in step a).

9. The process according to claim 1, wherein the molar ratio HBr:$C_1$-$C_3$ carboxylic acid in step b) is 1:1 to 1:10.

10. The process according to claim 1, wherein the molar ratio HBr:$C_1$-$C_3$ carboxylic acid in step b) is 1:2 to 1:4.

11. The process according to claim 1, wherein the temperature of mixture b) is in a range of above 10° C. and 40° C. or below.

12. The process according to claim 1, wherein said $C_1$-$C_3$ carboxylic acid is acetic acid.

13. The process according to claim 1, wherein said $C_1$-$C_3$ carboxylic acid is propionic acid.

14. The process according to claim 1, wherein said HBr and said $C_1$-$C_3$ carbolylic carboxylic acid together is 33 (w/w) % HBr dissolved in acetic acid.

* * * * *

UNITED STATES PATENT AND TRADEMARK OFFICE
CERTIFICATE OF CORRECTION

PATENT NO. : 11,124,491 B2
APPLICATION NO. : 16/604313
DATED : September 21, 2021
INVENTOR(S) : Hans Petersen It is certified that error appears in the above-identified patent and that said Letters Patent is hereby corrected as shown below:

In the Claims

Column 10, Line 60:
Claim 14, after "$C_1$-$C_3$" delete "carbolylic".

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*